US008183426B2

(12) United States Patent
Cole et al.

(10) Patent No.: US 8,183,426 B2
(45) Date of Patent: May 22, 2012

(54) DECONTAMINATING SHEET MATERIAL CONTAINING REACTIVE NANOCRYSTALLINE PARTICLES AND PRODUCTS CONSTRUCTED THEREFROM

(75) Inventors: Jason R. Cole, Arab, AL (US); Philip Mann, Langston, AL (US); Shyamala Rajagopalan, Manhattan, KS (US); Olga Koper, Manhattan, KS (US)

(73) Assignees: NanoScale Corporation, Manhattan, KS (US); Kappler, Inc., Guntersville, AL (US)

( * ) Notice: Subject to any disclaimer, the term of this patent is extended or adjusted under 35 U.S.C. 154(b) by 695 days.

(21) Appl. No.: 12/249,137

(22) Filed: Oct. 10, 2008

(65) Prior Publication Data

US 2009/0118562 A1    May 7, 2009

Related U.S. Application Data

(60) Provisional application No. 60/979,155, filed on Oct. 11, 2007, provisional application No. 60/979,156, filed on Oct. 11, 2007.

(51) Int. Cl.
*A62D 3/30* (2007.01)
(52) U.S. Cl. ........................................ 588/313; 502/439
(58) Field of Classification Search .................. 502/400, 502/401, 404, 439, 526; 588/313
See application file for complete search history.

(56) References Cited

U.S. PATENT DOCUMENTS

| 4,187,390 | A | 2/1980 | Gore |
| 4,777,073 | A | 10/1980 | Sheth |
| 4,257,997 | A | 3/1981 | Soehngen et al. |
| 4,350,655 | A | 9/1982 | Hoge |
| 4,791,144 | A | 12/1988 | Nagou et al. |
| 4,833,010 | A | 5/1989 | Langley |
| 4,868,062 | A | 9/1989 | Hoeschele et al. |
| 5,328,760 | A | 7/1994 | Gillberg-LaForce |
| 5,492,754 | A * | 2/1996 | Chen ............................ 442/398 |
| 5,594,070 | A | 1/1997 | Jacoby et al. |
| 5,637,165 | A * | 6/1997 | Chen ............................ 156/62.2 |
| 5,690,949 | A | 11/1997 | Weimer et al. |
| 5,759,939 | A | 6/1998 | Klabunde et al. |
| 5,865,926 | A | 2/1999 | Wu et al. |
| 5,914,436 | A | 6/1999 | Klabunde et al. |
| 6,057,488 | A | 5/2000 | Koper et al. |
| 6,410,465 | B1 | 6/2002 | Lim et al. |
| 6,417,423 | B1 | 7/2002 | Koper et al. |
| 6,827,766 | B2 | 12/2004 | Carnes et al. |
| 6,860,924 | B2 | 3/2005 | Rajagopalan et al. |
| 7,256,156 | B2 * | 8/2007 | Axtell et al. .................. 502/417 |
| 2002/0035032 | A1 | 3/2002 | Koper et al. |
| 2003/0216256 | A1 * | 11/2003 | Axtell et al. .................. 502/417 |
| 2004/0045479 | A1 | 3/2004 | Koper et al. |
| 2005/0084464 | A1 | 4/2005 | McGrath et al. |

FOREIGN PATENT DOCUMENTS

| WO | WO 2004/050001 | 6/2004 |
| WO | WO 2007/051145 | 5/2007 |

OTHER PUBLICATIONS

Examination Report for NZ Patent Application 568556 dated Feb. 3, 2010 (2 pgs).

* cited by examiner

*Primary Examiner* — Edward Johnson
(74) *Attorney, Agent, or Firm* — Hovey Williams LLP

(57) ABSTRACT

The invention provides a sorptive sheet material in which finely divided nanocrystalline particles that react with a variety of chemical and/or biological agents are dispersed. The sheet material comprises a fibrous web that is formed of a plurality of fibers that are bonded to each other. The fibrous web contains a relatively high concentration of reactive nanocrystalline particles that are entrapped within the matrix of the fibrous web. Fluids containing toxic agents, such as chemical and/or biological agents, odors and/or odor causing compounds, and toxic industrial compounds, pass into the web and contact the reactive nanocrystalline particles contained therein. The reactive nanocrystalline particles react with, and chemically alter or inactivate the toxic agents. The sorptive sheet material may be used to construct containers, such as remains pouches, for the storing and transporting of contaminated items, particularly human remains.

30 Claims, 2 Drawing Sheets

FIG. 2

DECONTAMINATING SHEET MATERIAL CONTAINING REACTIVE NANOCRYSTALLINE PARTICLES AND PRODUCTS CONSTRUCTED THEREFROM

RELATED APPLICATIONS

This application claims the benefit of U.S. Provisional Application Ser. No. 60/979,155, filed Oct. 11, 2007, and U.S. Provisional Application Ser. No. 60/979,156, filed Oct. 11, 2007, both of which are incorporated by reference herein.

FEDERALLY SPONSORED RESEARCH

This invention was made with United States Government support under contract W911NF-06-C-0060 awarded by the U.S. Army Research Office. The United States Government has certain rights in the invention.

FIELD OF THE INVENTION

This invention relates generally to materials for neutralizing chemical and biological agents, and in particular to a sheet material capable of neutralizing chemical and biological agents. The sheet material may also be used in the manufacture of products such as decontamination wipes, protective garments, filtration media, protective shelters, and remains pouches.

BACKGROUND OF THE INVENTION

It is estimated that more than 70 different chemicals have been used or stockpiled as chemical/biological weapon agents during the 20th century and the 21st century. Many of these agents can result in severe reactions in exposed individuals, including death. Some of the more familiar chemical/biological agents include nerve agents, such as sarin, soman, and tabun; vesicants, such as mustard gas and lewisite; and biological toxins, such as anthrax.

The risk of exposure to such chemical and biological agents is an ever increasing concern for military personnel as well as civilians. This concern is particularly heightened in view of recent terrorist attacks. In particular, terrorist threats involving such agents are increasing in the United States as well as abroad. For many terrorist organizations, chemical weapons might be considered an ideal choice for a mode of attack because of their potential to be widely dispersed to thereby maximize casualties. For example, on Mar. 20, 1995, Aum Shinirikyo, an apocalyptic group based in Japan released sarin into the Tokyo subway system killing 12 and injuring more than 5,000. Additionally, a skilled chemist can readily synthesize most chemical agents if the precursors are available.

Chemical/biological weapon agents are generally classified as persistent or nonpersistent according to the length of time they remain effective after dissemination. Agents classified as nonpersistent typically lose effectiveness after only a few minutes or hours. Purely gaseous agents such as chlorine are nonpersistent, as are highly toxic volatile agents such as sarin and most other nerve agents. By contrast, persistent agents can remain in the environment for an extended length of time, such as a week or longer. As a result, decontamination of effected areas and surfaces can be complicated and problematic. In particular, non-volatile liquid agents, such as blister agents and the oily VX nerve agent, do not easily evaporate into a gas, and therefore can present a contact hazard that can linger on an exposed surface long after an initial exposure.

For example, chemical agents can be present in the bodies and remains of humans for a significant duration of time following death. Further, biological toxins that have been introduced into a human being may remain potentially dangerous even after the host has been deceased.

In the context of human remains handling, under conventional practice, deceased individuals are stored and transported in remains vessels, commonly referred to as "body bags." Typically, such body bags are effective for their intended purposes under normal conditions. However, in circumstances involving exposure to chemical or biological agents, conventional body bags may not provide the desired level of containment. In particular, while the body bag provides protection to personnel handling the contaminated body or remains, the body/remains may still continue to carry the chemical and/or biological contamination, which can then be released if and when the bag is reopened. As a result, secondary exposure to the chemical and/or biological can occur.

In response to this threat, various countermeasures have been developed that are capable of neutralizing certain chemical/biological weapon agents. For example, decontamination formulations are available that utilize reactive nanoparticles to neutralize the effects of many of these agents by chemically destroying or otherwise altering the toxic nature of the agent. In general, such countermeasures are available in creams or lotions that can be applied to the skin, or as liquids or fogs/sprays that can be applied to exposed surfaces for neutralizing the chemical or biological agent. However, in such applications, the effectiveness of the decontamination formulation is limited by the ability to provide the neutralizing agent at the location of the chemical or biological agent and in a sufficient concentration for providing sustained protection. Accordingly, there exists a need for a system that can be used to effectively protect a surface from contact with chemical or biological agents, or that can be used to effectively decontaminate an exposed surface.

BRIEF SUMMARY OF THE INVENTION

The present invention provides a sorptive sheet material in which finely divided nanocrystalline particles that react with a variety of undesirable substances such as chemical and/or biological agents, odors and/or odor causing compounds, and toxic industrial compounds, are dispersed. The sheet material comprises a fibrous matrix in the form of a woven or nonwoven web that is formed of a plurality of fibers that are bonded to each other to form a strong and coherent sheet. Incorporated in the fibrous matrix is a relatively high concentration of reactive nanocrystalline particles that are entrapped within the matrix. Preferably, the fibrous matrix is in the form of a porous fibrous web. The particles may be sandwiched or entrapped in between layers of fibrous materials (i.e., trapped between quilted sheets). Fluids containing the undesirable substances pass into the web and contact the reactive nanocrystalline particles contained therein. The reactive nanocrystalline particles sorb, react with and/or chemically destroy or otherwise alter the nature of the toxic agents.

In one embodiment, the fibers forming the fibrous web comprise cellulosic fibers, including natural fibers such as cotton, linen, jute, hemp, wood pulp, etc. Among wood pulp fibers, any known papermaking fibers may be used, including softwood and hardwood pulp fibers. In a preferred embodiment, the sheet material is prepared in a wet-laid process in which an aqueous mixture or slurry of pulp fibers and reactive nanocrystalline particles is deposited on a forming surface to produce a web and the web is thereafter dried to produce a sheet material containing reactive nanocrystalline particles.

The concentration of the reactive nanocrystalline particles in the sheet material is typically from about 1 to 90 percent by weight, based upon the total weight of the sheet material, with a concentration of about 25 to 75 percent by weight, based upon the total weight of the sheet material being preferred.

Preferably, the reactive nanocrystalline particles have a surface area that is at least 15 m$^2$/g and an average crystallite size of up to about 40 nm. In certain embodiments, the particles may also have an average particle size that is up to about 150 nm. Suitable nanocrystalline particles that can be used in the practice of the invention include metal oxides, metal hydroxides, and combinations thereof. Exemplary nanocrystalline particles include $MgO$, $CeO_2$, $CaO$, $TiO_2$, $ZrO_2$, $FeO$, $V_2O_3$, $V_2O_5$, $Mn_2O_3$, $Fe_2O_3$, $NiO$, $CuO$, $Al_2O_3$, $ZnO$, $SiO_2$, $Ag_2O$, $SrO$, $BaO$, $Mg(OH)_2$, $Ca(OH)_2$, $Al(OH)_3$, $Sr(OH)_2$, $Ba(OH)_2$, $Fe(OH)_3$, $Cu(OH)_2$, $Ni(OH)_2$, $Co(OH)_2$, $Zn(OH)_2$, $AgOH$, doped metal oxides, (i.e., silver doped alumina, where the silver can be in an elemental or ionic state), halogen doped, or biocide incorporated metal oxides and mixtures thereof.

The sheet material of the present invention can be used in a wide variety of applications including protective garments, human remains pouches, filtration equipment, adsorptive pads and wipes and the like.

The sorptive sheets containing the finely divided nanocrystalline particles as described herein may be used in the construction of a remains pouch, such as a body bag, for the storage and transportation of contaminated bodies/remains. Fluids containing undesirable substances and/or toxic agents, such as chemical and/or biological agents, that are emitted by a body and/or remains pass into the sorptive sheet and contact the reactive nanocrystalline particles contained therein. The reactive nanocrystalline particles sorb, react with and/or chemically destroy or otherwise alter the nature of the toxic agents.

In one embodiment, the remains pouch comprises an envelope defining an interior for the placement of a human body and remains therein. The envelope includes an opening extending along a length of the envelope. The opening may be sealed with an associated gas-tight closure, such as a zipper-like structure, or the opening may be hermetically sealed through heat or through the use of an adhesive. Preferably, the envelope comprises a gas and liquid barrier material that is chemically resistant to the penetration of various chemical and/or biological agents including nerve agents, such as sarin, soman, and tabun; vesicants, such as mustard gas and lewisite; and biological toxins, such as anthrax. Preferably, the chemical barrier material exhibits breakthrough times greater than about 480 minutes for any one of mustard gas (HD), lewisite (L), tabun (GA), sarin (GB), Soman (GD), and nerve (VX) agents, when tested in accordance with 10 MIL-STD-282 methods 208 and 209.

As noted above, a sorptive sheet material is disposed in the interior of the pouch. The sheet material comprises a fibrous matrix and finely divided reactive metal oxide or metal hydroxide particles dispersed within the fibrous matrix, or the metal oxide particles can be sandwiched between the layers of the pad. Fluids draining from a body or remains disposed in the pouch are absorbed into said matrix so that undesirable substances contained in the fluids react with the nanocrystalline particles and are chemically destroyed or otherwise altered to render them nontoxic.

BRIEF DESCRIPTION OF THE DRAWINGS

Figure 1:
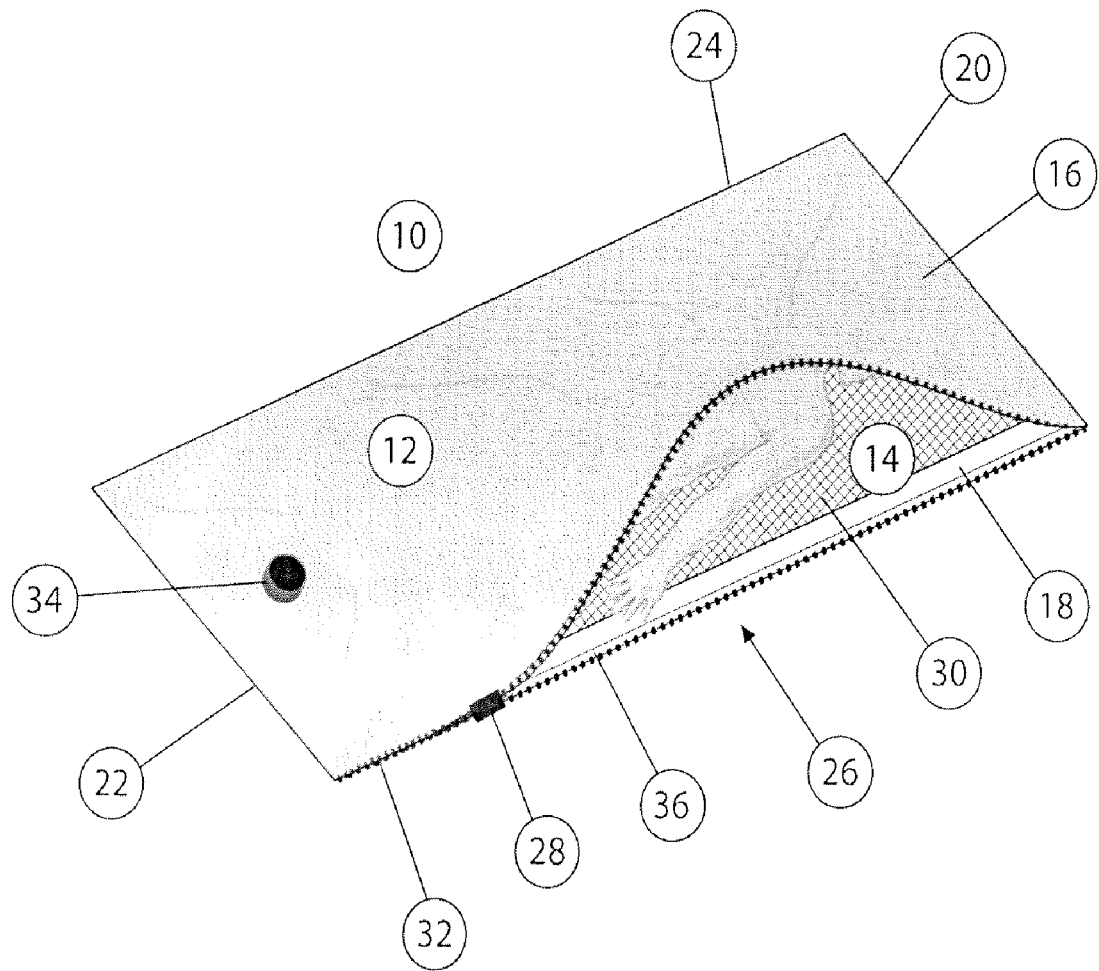

Having thus described the invention in general terms, reference will now be made to the accompanying drawings, which are not necessarily drawn to scale, and wherein:

FIG. 1 is an illustration of a lined pouch for containing a human body or remains that includes a sorptive pad having reactive metal oxide or metal hydroxide particles dispersed therein for neutralizing chemical and/or biological agents contained in fluids emitted by a human body or remains kept in the pouch; and FIG. 2 is a chart showing calculated GD concentration levels during tests on miniature remains pouches constructed in accordance with the present invention.

DETAILED DESCRIPTION OF THE INVENTION

The present invention now will be described more fully with reference to some specific illustrative embodiments. However, it is to be understood that the invention may be embodied in many different forms and should not be construed as limited to the embodiments set forth herein; rather, these embodiments are provided so that this disclosure will satisfy applicable legal requirements.

The present invention is directed to a sorptive sheet material comprising a fibrous matrix in which finely divided reactive metal oxide or hydroxide particles are dispersed and entrapped. The finely divided metal oxide or hydroxide particles comprise nanocrystalline particles that are capable of sorbing and neutralizing or chemically altering undesirable substances such as toxic agents like chemical and biological agents, odors and odor-causing compounds, and toxic industrial chemicals. As discussed in greater detail below, the sheet material of the present invention can be used in a wide variety of applications, such as protective garments, shelters, coverings, wipes, and the like.

As used herein, the term "chemical agents" includes but is not limited to chemical warfare agents such as blister or vesicant agents such as mustard agents, nerve agents such as methylphosphonothiolate (VX), lung damaging or choking agents such as phosgene (CG), agents such as cyanogen, hydrogen cyanide, incapacitants such as 3-quinuclidiniyl benzilate, riot control agents such as CS (malonitrile), smokes such as zinc chloride smokes, and some herbicides such as 2,4-D (2,4-dichlorophenoxy acetic acid).

As used herein, the term "biological agents" includes but is not limited to biological materials such as bacteria, fungi, viruses, and toxins that may be used as biological warfare agents. Exemplary bacteria include *Bacillus anthracis* (anthrax), *Yersinia pestis* (plague), gram positive bacteria like *B. subtilis*, *B. globigii*, and *B. cereus*, or gram negative bacteria like *E. coli* and *E. Herbicola*. Exemplary viruses include variola virus (small pox) and flaviviruses (hemorrhagic fevers). Exemplary toxins include botulinum toxins, saxitoxin, Aflatoxins, *Clostridium perfringens* toxins, Conotoxins, Ricins, Saxitoxins, Shiga toxins, *Staphylococcus aureus* toxins, Tetrodotoxins, Verotoxins, Microcystins (Cyanginosin), Abrins, Cholera toxins, Tetanus toxins, Trichothecene mycotoxins, Modeccins, Volkensins, Viscum Album Lectin 1, Streptococcal toxins (e.g., erythrogenic toxin and streptolysins), *Pseudomonas* A toxins, Diphtheria toxins, Listeria monocytogenes toxins, *Bacillus anthracis* toxic complexes, *Francisella tularensis* toxins, whooping cough pertussis toxins, *Yersinia pestis* toxic complexes, *Yersinia enterocolytica* enterotoxins, and *Pasteurella* toxins.

Exemplary odors and odor causing compounds include animal odors, animal waste odors, asphalt fumes, charred materials, cleaning chemicals, decaying bodies, decaying vegetation, detergents, diapers, exhaust, fuel (i.e., gasoline/diesel), volatile organic compound fumes (e.g., paint, varnish, and solvent odors), odors caused by moisture or flooding (i.e., mold and mildew), human body odors (i.e., sweat, bacterial infections, urine and fecal odors) hunting odors (i.e., deer urine), kitchen odors (i.e., refrigerator odors, burnt food, cooking odors, fish, poultry, garlic, onion, rancid oils), medicinal odors, sewer gases, smoke (e.g., tobacco smoke odors) and garbage. Further compounds are disclosed in International Patent Application Publication WO 2007/051145, incorporated by reference herein.

As used herein, the term "toxic industrial chemicals" or "TICs" refers to industrial chemicals in the gas, liquid, or solid state which may be commonly found in chemical plants, industrial manufacturing facilities, waste water treatment plants, chemical/waste storage facilities/landfills, laboratory settings, large fuel storage areas, and at major transportation centers including the vehicles (trains, barges, etc.). They can be chemical hazards (e.g., carcinogens, reproductive hazards, corrosives, or agents that affect the lungs or blood) or physical hazards (e.g., flammable, combustible, explosive, or reactive). Exemplary TICs include: ammonia, acetone cyanohydrin, allyl isothiocyanate, arsine, acrolein, arsenic trichloride, boron trichloride, acrylonitrile, bromine, boron trifluoride, allyl alcohol, bromine chloride, carbon disulfide, allylamine, bromine pentafluoride, chlorine, allyl chlorocarbonate, bromine trifluoride, diborane, boron tribromide, carbonyl fluoride ethylene oxide, carbon monoxide, chlorine pentafluoride, fluorine, carbonyl sulfide, chlorine trifluoride, formaldehyde, chloroacetone, chloroacetaldehyde, hydrogen bromide, chloroacetonitrile, chloroacetyl chloride, hydrogen chloride, chlorosulfonic acid, crotonaldehyde, hydrogen cyanide, diketene, cyanogen chloride, hydrogen fluoride, 1,2-dimethylhydrazine, dimethyl sulfate, hydrogen sulfide, ethylene dibromide, diphenylmethane-4.4'-diisocyanate, nitric acid (fuming), hydrogen selenide, ethyl chloroformate, phosgene, methanesulfonyl chloride, ethyl chlorothioformate, phosphorus trichloride, methyl bromide, ethyl phosplhonothioic dichloride, sulfur dioxide, methyl chloroformate, ethyl phosphonic dichloride, sulfuric acid, methyl chlorosilane, ethyleneimine, tungsten hexafluoride, methyl hydrazine, hexachlorocyclopentadiene, methyl isocyanate, hydrogen iodide, methyl mercaptan, iron pentacarbonyl, nitrogen dioxide, isobutyl chloroformate, phosphine, isopropyl chloroformate, phosphorus oxychloride, isopropyl isocyanate, phosphorus pentafluoride, n-butyl chloroformate, selenium hexafluoride, n-butyl isocyanate, silicon tetrafluoride, nitric oxide, stibine, n-propyl chloroformate, sulfur trioxide, parathion, sulfuryl fluoride, perchloromethyl mercaptan, tellurium hexafluoride, sec-butyl chloroformate, n-octyl mercaptan, tert-butyl isocyanate, titanium tetrachloride, tetraethyl lead, tricholoroacetyl chloride, tetraethyl pyrophosphate, trifluoroacetyl chloride, tetramethyl lead, toluene 2,4-diisocyanate, and toluene 2,6-diisocyanate.

The fibrous matrix is formed of a plurality of fibers that form a fibrous matrix through which fluids (i.e., liquids and gases) are able to pass. Preferably, the fibrous matrix is in the form of a fibrous web that is capable of absorbing and retaining fluids. In certain embodiments, the nanocrystalline particles are homogeneously dispersed and entrapped throughout the fibrous web or fibrous matrix so that fluids containing chemical and/or biological agents come in contact with the reactive nanocrystalline particles distributed throughout the sheet material. The nanocrystalline particles may be bonded to the fibrous matrix with a binding material such as an adhesive, through electrostatic attachment, or by physically entrapping the particles within the network of fibers making up the fibrous matrix. In addition, the nanocrystalline particles may be sandwiched in between adjacent layers of woven or non-woven material making tip the fibrous matrix.

The reactive nanocrystalline particles react with the chemical and/or biological agents to alter the chemical structure and thereby render them nonhazardous. The fibrous web is capable of containing a relatively high concentration of the reactive nanocrystalline particles. The concentration of the reactive nanocrystalline particles in the sheet material is typically from about 1 to 90 percent by weight, based upon the total weight of the sheet material, with a concentration from about 25 to 75 weight percent being preferred, and from about 40 to 60 weight percent being more preferred. In some advantageous embodiments, the concentration of reactive nanocrystalline particles in the sheet material is about 50 percent by weight, based upon the total weight of the sheet material. The fibrous web presents a porous structure through which the chemical or biological agents can penetrate so as to readily come into contact with the reactive nanocrystalline particles.

The fibers forming the fibrous web can be made from a variety of materials including natural fibers, synthetic fibers, and combinations thereof. In general, the choice of fibers depends upon, for example, the intended end use of the finished fabric and fiber cost. For instance, suitable fibrous substrates may include, but are not limited to, natural fibers such as cotton, linen, jute, hemp, wool, wood pulp, etc. For reasons of cost, ready availability and absorbency, wood pulp fibers are particularly well suited for use in producing the fibrous web. Among wood pulp fibers, any known papermaking fibers may be used, including softwood and hardwood fibers. Fibers, for example, may be chemically pulped or mechanically pulped, bleached or unbleached, virgin or recycled, high yield or low yield, and the like. Mercerized, chemically stiffened or crosslinked fibers may also be used. In one embodiment, the fibrous web is composed of wood pulp fibers having a length between about 1 and 10 mm.

In some embodiments, regenerated cellulosic fibers, such as viscose rayon and cuprammonium rayon, modified cellulosic fibers, such as cellulose acetate, or synthetic fibers, such as those derived from polypropylenes, polyethylenes, polyolefins, polyesters, polyamides, polyacrylics, etc. may likewise be used alone or in combination with one another or with wood pulp fibers. Blends of one or more of the above fibers may also be used, if so desired. Synthetic cellulose fiber types include rayon in all its varieties and other fibers derived from viscose or chemically modified cellulose, including regenerated cellulose and solvent-spun cellulose, such as Lyocell.

The basis weight of the fibrous web generally varies dependent on the intended use of the sheet material. For example, in applications in which the sheet material comprises a wipe product, the basis weight of the fibrous web is from about 0.5 to 50 ounces per square yard (oz/sq yd), whereas in protective garment applications the fibrous web has a basis weight that is from about 1 to 30 oz/sq yd, and more preferably between about 1.5 and 10 oz/sq yd, based on the total weight of the sheet material. Similarly, the thickness of the sheet material can also vary depending on the intended use of the sheet material. Typically, the thickness of the sheet material ranges from about 1 to 250 mils, and more preferably from about 1 to 50 mils for protective garment applications, and from about 50 to 150 mils for absorbent wipe applications.

Preferably, the reactive nanocrystalline particles have a sufficient surface area for reacting with various chemical/biological agents to which they come in contact with. Preferably, the reactive nanocrystalline particles have a Brunauer-Emmett-Teller (BET) multipoint surface area that is at least 15 $m^2/g$, preferably at least about 100 $m^2/g$, and more preferably, about 200 $m^2/g$ or more. In certain embodiments, the reactive nanocrystalline particles have an average crystallite size that is below about 20 nm. The nanocrystalline particles can be present as discrete individual nanocrystalline particles or as clusters of nanocrystalline particles.

Suitable nanocrystalline particles that can be used in the practice of the invention include metal oxides, metal hydroxides, and combinations thereof. Exemplary nanocrystalline particles include $MgO$, $CeO_2$, $CaO$, $TiO_2$, $ZrO_2$, $FeO$, $V_2O_3$, $V_2O_5$, $Mn_2O_3$, $Fe_2O_3$, $NiO$, $CuO$, $Al_2O_3$, $ZnO$, $SiO_2$, $Ag_2O$, $SrO$, $BaO$, $Mg(OH)_2$, $Ca(OH)_2$, $Al(OH)_3$, $Sr(OH)_2$, $Ba(OH)_2$, $Fe(OH)_3$, $Cu(OH)_2$, $Ni(OH)_2$, $Co(OH)_2$, $Zn(OH)_2$, $AgOH$, and mixtures thereof. Exemplary nanocrystalline particles that may be used in the practice of the invention are discussed in greater detail in U.S. Pat. Nos. 5,759,939, 5,914,436, 6,057,488 and 6,417,423 and U.S. Patent Publication Nos. 2002/0035032 and 2004/0045479, the contents of which are hereby incorporated by reference in their entireties.

The reactive nanocrystalline particles can be used alone, such as in a powder form, or can be modified to include additional reactive sites on their surfaces. For example, in one embodiment, the reactive nanocrystalline particles may comprise metal oxide or metal hydroxides having reactive atoms (different from those atoms malting up the metal oxide) disposed on at least a portion of their surfaces. In general, the particles should have the same average particle sizes and surface areas described above. Preferably, the reactive atoms utilized in this embodiment are selected from the group consisting of halogens and Group I metals. When halogens are the reactive atoms being stabilized on the surfaces of the particles, the atoms can be atoms of the same halogen (e.g., only chlorine atoms), or the atoms can be mixtures of atoms of different halogens (e.g., both chlorine and bromine atoms on the metal oxide surfaces).

In another embodiment, the nanocrystalline particles comprise metal oxide particles coated with a second, different metal oxide. For example, the coated metal oxide particles comprise a first metal oxide selected from the group consisting of $MgO$ and $CaO$ that is coated with a second metal oxide such as $ZnO$. In yet another embodiment, the first metal oxides described above are coated with a mixture of metal nitrates such as those selected from the group consisting of $Cu(NO_3)_2$, $Ce(NO_3)_3$, $AgNO_3$, $Zn(NO_3)_2$ and mixtures thereof. In a further embodiment, $TiO_2$ is coated with a mixture of cerium nitrate and copper nitrate to form $[Ce(NO_3)_3\text{---}Cu(NO_3)_2]TiO_2$.

In still other embodiments, the nanocrystalline particles comprise doped metal oxides, such as silver doped alumina, and metal oxide or metal hydroxide particles impregnated with a biocide as described in U.S. Pat. No. 6,827,766, incorporated by reference herein. In yet other embodiments, the nanocrystalline particles may be coated with a material such as surfactants, waxes, oils, silyls, synthetic and natural polymers, resins, and mixtures thereof as described in U.S. Pat. No. 6,860,924, incorporated by reference herein.

Other reactive particles that can be used in the sheet material include reactive silver nanocrystalline particles that are available from several sources, such as a powder of elemental silver nanocrystalline particles sold under the name Effisil from NovaCentri Corp. of Austin Tex., or as metal doped metal oxide nanoparticles, such as silver doped aluminum oxide. The presence of the silver particles, either in metallic or ionic form, can be used to neutralize a wide variety of biological agents. When present, the concentration of silver is typically between about 0.1 to 30 weight percent, and more typically, from about 1 to 20 weight percent, based on the total weight of the metal oxide, or hydroxide. In one embodiment, the silver particles comprise nanocrystalline particles that are homogeneously dispersed in the fibrous web, and have a particle size from about 2 to 1000 nm, and more preferably from 10 to 100 nm.

In addition to the reactive nanocrystalline particles, the fibrous web may also include additives, such as binders, stabilizers, fillers, pigments and the like.

The sheet material of the present invention can be formed in a wide variety of manners. In a preferred embodiment, a wet-laid process is utilized in which the reactive nanocrystalline particles are entrapped in a fibrous matrix of fibers. In a wet-laid process, an aqueous slurry containing cellulosic fibers, reactive nanocrystalline particles, and any additional additives/fillers is fed into a headbox which ejects the stock onto a forming wire. Water is then drained from the thus formed web through the forming wire so that a wet web of paper is formed on the wire and the web is further dewatered in the press section and dried in the drying section of the paper machine. The resulting sheet material comprises a paper-like substrate in which the reactive nanocrystalline particles are dispersed. For some embodiments, the sheet material can be optionally calendered.

The sorptive sheet material of the present invention can be used in a wide variety of applications in which protection from exposure to undesirable substances is desirable. For example, the sorptive sheet material can be used in the fabrication of protective garments, such as suits, gloves, headwear, jackets, boots, and the like. The sheet material can also be used advantageously in the production of protective shelters for humans and animals as well as the productions of coverings for protecting buildings and equipment. The sheet material can also be provided in the form of a filter medium that can be used in the filtration of fluids, such as liquids and gases, to thereby neutralize chemical and/or biological agents carried therein. In a further embodiment, the sorptive sheet material can also be in the form of a disposable or non-disposable (i.e., reusable) wipe or pad that can be used to clean/remove fluids containing chemical and/or biological agents. In still other embodiments, the sorptive sheet material can also be used as a packing material in the transport of ordinance or used chemical handling equipment (e.g., from a meth lab that has been seized by law enforcement). The sorptive sheet material protects against accidental release of agent from the ordinance being transported or from the chemical handling equipment.

The sorptive sheet material can also be combined with one or more additional layers in a laminate structure. For example, the sheet material can be attached to one or more layers comprising a woven or nonwoven fabric. In one particular embodiment, a protective garment comprising an outer barrier layer and inner layer comprising the sorptive sheet material of the present invention can be provided.

In other embodiments, one or more layers of the sheet material can be combined with one or more layers of a vapor permeable, liquid impermeable film. Examples of vapor permeable, liquid impermeable films include monolithic permeable films and microporous films. Monolithic permeable films are typically formed from a polymer selected from the group consisting of polyester, copolyester, polyurethane, copolyether ester, copolyether amide, copoly(etherimide)ester and/or blends thereof. Commercial examples of such materials include Aptra M (RKW GmbH), and films like Sympatex® which is made from a monolithic copolyester ether resin film. Lim (U.S. Pat. No. 6,410,465), incorporated herein by reference, discloses several other types of waterproof/breathable films and membranes such as copolyether ester block copolymers such as Hytrel® (DuPont), polyetherblock co-polyamide polymers such as Pebax® (Atofina Chemicals), thermoplastic polyurethanes such as Estane® (Noveon Inc.), Dynapol® and Dynacoll® (Creanova, Inc.), and copoly(etherimide)esters as described by Hoechst (U.S. Plat. No. 4,868,062). Other examples of vapor permeable, liquid impermeable films include microporous films that offer air impermeability, liquid resistance, and high degrees of moisture vapor transmission through various microporous structures. Processes for producing the micropores vary and include cold rolling, and stretching (mono-axially, biaxially, and incrementally) filled films. For stretched films, the mechanism for cavitation can include a solid particle (i.e., calcium carbonate) that will remain in the film after stretching or a soluble component (i.e., mineral oil) that can be extracted after stretching thus leaving the void. Microporous films are disclosed for example in Hoge U.S. Pat. No. 4,350,655, Sheth U.S. Pat. No. 4,777,073, Wu et al. U.S. Pat. No. 5,865,926, Soehngen et al. U.S. Pat. No. 4,257,997, Gillberg-LaForce U.S. Pat. No. 5,328,760, Nagou et al. U.S. Pat. No. 4,791,144, Jacoby U.S. Pat. No. 5,594,070, Gore U.S. Pat. No. 4,187,390, Weimer et al. U.S. Pat. No. 5,690,949. In one embodiment, the sorbent sheet material of the present invention is positioned on one or both sides of a vapor permeable, liquid impermeable film to form a laminate. In other embodiments, the sorbent sheet material is positioned between two vapor permeable, liquid impermeable films.

The sorbent sheet material may also be used in the construction of a contaminated remains pouch, such as a "body bag," for containing a human body or remains that have been exposed to chemical and/or biological agents. FIG. 1 illustrates a contaminated remains pouch 10 comprising an envelope 12 defining an interior 14 for the placement of a human body and remains therein. As shown, the envelope is depicted in a partially open state and a human body is disposed in the interior of the pouch.

In the illustrated embodiment, the envelope 12 comprises a top sheet 16 and a bottom sheet 18 that are oriented face-to-face and affixed to each other at top and bottom edges 20, 22 and side edge 24. Preferably, each of the top and bottom edges and side edge are hermetically sealed to each other. In some embodiments the top and bottom sheets may comprise two separate sheets, or alternatively, a single sheet that has been center-folded at side edge 24. Together the sheets define interior 14 having an interior space for receiving a body and/or remains and a pouch opening 26 through which the body/remains can be placed into the interior of the pouch. In a preferred embodiment, the opening extends at least partially along the length of the envelope. A gas-tight closure 28 for sealably closing the opening is disposed along the opening. A sorptive sheet material 30 for absorbing fluids emitted by a body or remains is disposed in the interior of the envelope. As briefly noted above, the sheet material comprises a fibrous matrix in which finely divided reactive nanocrystalline particles are dispersed. In the illustrated embodiment, the sorptive sheet material 30 is depicted as being positioned beneath a human body that is disposed in the pouch.

In the illustrated embodiment, the opening 26 is depicted as extending along side edge 32 that is defined by closure 28 when the opening of the envelope is closed. It should be recognized that the exact position of the closure is not critical to the invention provided that the opening can accommodate the introduction and removal of a body and/or remains from the interior of the pouch 10. For example, the top and bottom sheets of the envelope can be sealed to each other along all adjacent edges and the opening can extend along a length of the envelope between opposite side edges. Alternatively, one of the top or bottom edges of the envelope can be open to define an opening into the interior of the pouch. In this embodiment, the body/remains can be inserted head or feet first.

The illustrated embodiment also comprises a liner section 36 disposed proximate pouch opening 26 and closure 28. The liner section 36 is generally disposed in a covering relationship to closure 28 upon sealing of the opening to prevent the escape of toxic materials therefrom. The liner section 36 may be constructed with the same sorptive sheet material 30 positioned beneath the body or remains, or the liner section 36 may comprise a different embodiment of the sorptive sheet material containing nanocrystalline particles described herein. While not necessarily essential to all embodiments of the present invention, the benefits achieved when utilizing liner section 36 in certain applications are described in Example 2 below.

The embodiment illustrated in FIG. 1 also includes an optional cartridge 34 that may be included in those pouches to be used in air transportation of remains. In flight, the cabin pressure within the aircraft is likely to be different than the air pressure within pouch 10 at the time the remains were placed inside and opening 26 sealed. Further, decomposition gases may also build up within the pouch, thereby creating another overpressure concern. In one embodiment, cartridge 34 is a filtered exhaust valve and venting device that allows pouch 10 to be used in hyperbaric conditions and permits venting decompositions gases that may build up within the pouch. Cartridge 34 is sealed into pouch 10 with two reinforced gaskets and includes a zero pressure flapper valve and multi-vented cap which eliminates the possibility of over-pressurization of the pouch. Cartridge 34 may be configured to permit one-way or two-way communication between the pouch exterior and the pouch interior 14. Cartridge 34 may also be provided with a filter comprising the same types of nanocrystalline particles that may be used in sorptive sheet material 30. Thus, toxic materials contained in the gas to be vented can be removed, or their concentration reduced to safe levels, prior to being exhausted to the surrounding atmosphere through cartridge 34. In embodiments of the present invention designed for ground or sea transport, cartridge 34 is not required to be present in pouch 10.

Preferably, the envelope is formed from a chemical barrier fabric that is substantially impervious to gases and liquids, and that has a high chemical permeation resistance. In a preferred embodiment, the chemical barrier fabric exhibits breakthrough times greater than about 480 minutes for any one of mustard gas (HD), lewisite (L), tabun (GA), sarin (GB), Soman (GD), and nerve (VX) agents, when tested in accordance with 10 MIL-STD-282 methods 208 and 209.

In one embodiment, the chemical barrier fabric comprises a multilayered film comprised of one or more resins selected from the group consisting of polyvinyl chloride (PVC), chlorinated polyethylene, chlorinated butyl polyethylene, high density polyethylene, low density polyethylene, linear low density polyethylene, polypropylene, polyurethane, polytetrafluoroethylene (PTFE), and combinations thereof. In some embodiments, the chemical barrier fabric can comprise one or more of ethylene-vinyl acetate, ethylene vinyl alcohol, polyvinyl alcohol, nylon, ionomers, such as Surlyn®, polyester, and the like.

Suitable chemical barrier fabrics that may be used in the practice of the invention are described in U.S. Pat. No. 4,833,010 and U.S. Patent Publication No. 2001/0051481 the contents of which are hereby incorporated by reference. An exemplary chemical barrier fabric that may be used in the practice of the invention is the Zytron® family of products, which is available from Kappler, Inc. of Guntersville, Ala.

As noted above, the envelope includes a gas-tight closure 28 for closing and sealing the opening 26. In one embodiment, the closure comprises a "zipper-like" structure that is configured to seal the pouch and thereby prevent contaminated fluids from escaping out of the interior of the pouch. Suitable materials that can be used for the zipper include PVC, polyethylene, polypropylene, butyl rubber, polychloroprene rubbers, such as neoprene, thermoplastic elastomers, such as Hytrel®, and the like. An exemplary closure that can be used in the practice of the invention comprises a gas-tight PVC zipper that is commercially available from YKK®. Preferably, the opposing elements of the zipper-like closure are each hermetically sealed to adjacent edges of the chemical barrier fabric along the opening of the envelope. An hermetic seal may also be created by heat sealing the opening or providing an adhesive, such as a pressure sensitive adhesive, on one or more portions of the pouch opening.

The envelope can be formed in any conventional manner provided fluids, such as gases and liquids, cannot escape from the interior of the pouch. As noted above, the envelope can be formed from a single sheet that is center-folded on itself to define top and bottom sheets, or from two separate sheets that are oriented in a juxtaposed relation, and are sealed along adjacent opposing edges. Preferably, the edges of the pouch are hermetically sealed to each other to thereby prevent the escape of fluids from the interior of the pouch.

It should be recognized that a wide variety of different remain pouches, such as body bags, can be used in the practice of the invention provided the pouches are constructed of a chemical resistant material and are able to be sealed to prevent the ingress and egress of fluids into or out of the pouch. An exemplary remains pouch that may be used in the practice of the invention is described in PCT Publication No. WO 04/050001 A2, the content of which is hereby incorporated by reference.

The thickness of the sorptive sheet material can be selected, at least in part, on the typical volume of bodily fluids that can be expected to be emitted by a contaminated body. Generally, the sorptive sheet material has a thickness in the range from 1 to 250 mils and a basis weight from about 0.5 to 50 ounces per square yard. The dimensions of the sorptive sheet material can also be selected based on the desired surface area from which fluids are to be absorbed. In one embodiment, the sorptive sheet material has a size and shape that approximates the size and shape of one of the sides of the pouch. For example, in the illustrated embodiment, the size and shape of the sorptive sheet material can be selected to approximate the size and shape of at least one of the top or bottom sheets. In some embodiments, the sorptive sheet material can be in the form of a liner that substantially lines the inner surface of the pouch so that a body disposed therein is surrounded by the sorptive sheet material. The sorptive sheet material can be attached to an inner surface of the pouch or can be placed in the pouch in a relatively loose and unencumbered manner.

The pouch of the present invention can also be used as container for storing and transporting other contaminated items, such as forensic samples, soil samples, water samples, gas samples and the like.

The following examples are provided for demonstrating the ability of the sorptive sheet material to neutralize chemical agents. The examples are not intended to limit the invention in any way.

EXAMPLES

Example 1

Sorbent disks having a diameter of 11 cm were prepared by adding approximately 4.8 grams of bleached shredded copy paper to approximately 300 mL of water. The mixture was blended together at high speed for about 2 minutes to create an aqueous slurry to which about 4.8 grams of FAST-ACT nanocrystalline particles (from NanoScale Corporation, Manhattan, Kans.) were added. The FAST-ACT nanocrystalline particles were present in clusters with an overall cluster size of about 4.8 micrometers. The mixture was further blended for an additional 3-4 seconds. The resulting solution was poured into a 11 cm Buchner funnel with an 11 cm piece of 0.75 oz/square yard spunbond polypropylene to act as a filter. The funnel was placed into a 1000 mL flask with a vacuum outlet to remove the excess water. The pulp was then removed and allowed to dry for 48 hours at ambient conditions. The resulting pad was then tested by Miller-Nelson Analytical of Leesburg, Fla. for simulated chemical agent testing. Sorbent pads containing no nanocrystalline particles were produced under the same conditions to serve as a control. The difference in weight of the control vs. the samples is attributed to the weight of the nanocrystalline particles and any residual moisture. The sorbent pads were tested in accordance with NFPA 1994 (normalized). The results are summarized in the tables below. In Tables 1-3, chloroethyl ethyl sulfide (CEES) was used as the challenge chemical. CEES is a common surrogate for mustard gas. In Tables 4, 5 and 6 dimethyl methylphosphonate (DMMP) was used as the challenge chemical. Flame ionization detection was used for both tests. DMMP is a common surrogate for sarin nerve gas.

TABLE 1

Blank Paper Control (no particles)

| Test Results | Test 1 | Test 2 | Test 3 | Average |
| --- | --- | --- | --- | --- |
| Normalized breakthrough time, min | 1 | 1 | 1 | 1 |
| Steady state permeation µg/sq cm/min | 128.9 | 79.6 | 125.0 | 111.1 |
| Thickness, mils | 65.1 | 59.5 | 53.1 | 59.2 |
| Weight oz/sq yd | 12.0 | 10.8 | 11.8 | 11.5 |

TABLE 2

Paper Containing $Al_2O_3$ nanocrystalline particles

| Test Results | Test 1 | Test 2 | Test 3 | Average |
| --- | --- | --- | --- | --- |
| Normalized breakthrough time, min | 3 | 5 | 5 | 4 |
| Steady state permeation µg/sq cm/min | 1.87 | 0.36 | 0.29 | 0.84 |
| Thickness, mils | 93.4 | 166.6 | 107.3 | 122.4 |
| Weight oz/sq yd | 29.5 | 29.6 | 29.7 | 29.0 |

TABLE 3

Paper Containing $TiO_2$ nanocrystalline particles

| Test Results | Test 1 | Test 2 | Test 3 | Average |
| --- | --- | --- | --- | --- |
| Normalized breakthrough time, min | 3 | 1 | 3 | 2 |
| Steady state permeation µg/sq cm/min | .56 | 5.62 | 0.32 | 2.17 |
| Thickness, mils | 100.7 | 84.9 | 107.6 | 97.7 |
| Weight oz/sq yd | 27.6 | 25.9 | 29.7 | 27.8 |

TABLE 4

Blank Paper Control (no particles)

| Test Results | Test 1 | Test 2 | Test 3 | Average |
|---|---|---|---|---|
| Normalized breakthrough time, min | 2 | 2 | 2 | 2 |
| Steady state permeation µg/sq cm/min | 10.33 | 6.24 | 9.04 | 8.54 |
| Thickness, mils | 74 | 63 | 66.4 | 67.8 |
| Weight oz/sq yd | 13.0 | 11.9 | 12.2 | 12.4 |

TABLE 5

Paper Containing $Al_2O_3$ nanocrystalline particles

| Test Results | Test 1 | Test 2 | Test 3 | Average |
|---|---|---|---|---|
| Normalized breakthrough time, min | >240 | >240 | >240 | >240 |
| Steady state permeation µg/sq cm/min | ND | ND | ND | ND |
| Thickness, mils | 100.9 | 86.9 | 106.6 | 98.1 |
| Weight oz/sq yd | 28.4 | 27.3 | 28.6 | 28.1 |

TABLE 6

Paper containing $TiO_2$ nanocrystalline particles

| Test Results | Test 1 | Test 2 | Test 3 | Average |
|---|---|---|---|---|
| Normalized breakthrough time, min | >240 | >240 | >240 | >240 |
| Steady state permeation µg/sq cm/min | ND | ND | ND | ND |
| Thickness, mils | 94.1 | 105.2 | 106.9 | 101.2 |
| Weight oz/sq yd | 26.0 | 26.8 | 28.2 | 27.0 |

Example 2

In this example, swatches of constructs with and without nanocellulose paper containing FAST-ACT particles were tested to determine efficacy in preventing the permeation of actual chemical warfare agents (CWAs), particularly HD and GD. The swatches tested were of various constructions. A first swatch containing a seam was constructed by sewing together two pieces of Zytron® 500 material. At the seam, a barrier tape was heat-sealed to the fabric. A second sewn swatch was constructed in a similar fashion except that a layer of nanocellulose paper made with the FAST-ACT particles was layered on top of the Zytron® 500 material. A third swatch was constructed of the same materials of the first swatch, however, the seam was replaced with a zipper. The same interface techniques were used as are typically used in construction of Zytron® 500 suits and contaminated remains pouches (CRPs). A fourth swatch was constructed similar to the third swatch except that a layer of nanocellulose paper made with the FAST-ACT particles was layered on top of the Zytron® 500 material.

All the swatch testing followed the liquid challenge/vapor permeation test method developed by the Aerosol, Vapor, and Liquid Assessment Group (AVLAG) for use in material testing as described in the U.S. Army Test and Evaluation Command (ATEC) Test Operations Procedure (TOP) 8-2-501 (incorporated by reference herein) and was carried out at the Hazardous Materials Research Center, Battelle Memorial Institute, West Jefferson, Ohio.

As shown in Table 7, the seam-containing swatches with and without the nanocellulose paper containing the FAST-ACT particles were adequate for withstanding CWAs.

TABLE 7

96-hour Cumulative Permeation Data from Seam Containing Swatches

| Sample | HD (µg/cm$^2$) | GD (µg/cm$^2$) |
|---|---|---|
| Negative control (without any deposited agent) | 1.06 | 0.69 |
| Seam-containing swatch | 1.11 | 0.69 |
| FAST-ACT integrated seam containing swatch | 1.09 | 0.69 |

Test conditions: Swatch test area = 10 cm$^2$; Amount of agent used = 1020 µg/cm$^2$; Test procedure = modeled after TOP 8-2-501; Test duration = 96 h.

However, as the results in Table 8 demonstrate, the zipper area requires more protection. In this instance, the presence of the nanocellulose paper containing the FAST-ACT particles shows greatly improved performance versus the swatch without the nanocrystalline particle-containing paper layer.

TABLE 8

96-hour Cumulative Permeation Data from Zipper Containing Swatches

| Sample | HD (µg/cm$^2$) | GD (µg/cm$^2$) |
|---|---|---|
| Negative control (without any deposited agent) | 1.06 | 0.69 |
| Zipper-containing swatch | 289 | 63.08 |
| FAST-ACT integrated zipper-containing swatch | 7.82 | 0.69 |
| % Reduction in agent permeation | >97% | >98% |

Test conditions: Swatch test area = 10 cm$^2$; Amount of agent used = 1020 µg/cm$^2$; Test procedure = modeled after TOP 8-2-501; Test duration = 96 h.

Miniature remains pouches were constructed using the above materials and tested for their resistance to CWA permeation. Levels of CWA were measured both within the pouch and in a confined space outside of the pouch. Results of this testing are provided in Table 9 and FIG. 2. The miniature remains pouch containing a nanocellulose liner including the FAST-ACT particles was highly effective in mitigating CWA hazards inside the pouch. A dramatic reduction in the amount of permeated GD both inside the pouch and through the pouch into the external environment was seen.

TABLE 9

GD Permeation Data for Miniature Pouch Systems

| | GD (mg/m$^3$) | |
|---|---|---|
| Sample | inside the pouch | outside the pouch |
| Control miniature pouch | 8.5 (2 h); 11 (5 h); 19 (9 h); 39 (25 h); 49 (49 h), 46 (72 h); and 46 (96 h) | $2.41 \times 10^{-5}$ to $2.03 \times 10^0$ |
| FAST-ACT integrated miniature pouch | 0.62 (2 h); 0.42 (4 h); 1.0 (12 h); 0.20 (24 h); <0.26 (48, 72 and 96 h) | $1.71 \times 10^{-5}$ to $3.60 \times 10^{-4}$ |

Test conditions: Pouch dimensions = 42 × 22 × 7"; Amount of agent used = 149.8 mg; Test duration = 96 h.

It should be noted from FIG. 2 for the standard miniature pouch that the calculated GD concentration in the confined space exceeded the 30 minute AEGL-1 (Acute Exposure Guideline Level) after ca. 40 hours (30 minute AEGL-1 being 0.0020 mg/m$^3$. In stark contrast, within the enhanced pouch the calculated concentration in the confined space never exceeded the 30 minute AEGL-1 and stayed well below this level during the entire test period (FIG. 2).

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

We claim:

1. A pouch for the containment of human bodies or remains, the pouch comprising:
    a sorptive sheet material comprising a fibrous matrix and finely divided, nanocrystalline reactive particles dispersed within and bonded to the fibrous matrix,
    an envelope defining an interior for the placement of a human body or remains therein, the envelope having an opening extending along a length of the envelope and being formed from a gas and liquid barrier material,
    the sorptive sheet material being disposed in the interior of the pouch, wherein fluids emitted by a body or remains kept in said pouch are absorbed into said fibrous matrix and come into contact with the reactive nanocrystalline particles.

2. The pouch of claim 1, wherein the finely divided nanocrystalline reactive particles are selected from the group consisting of nanocrystalline metal particles, nanocrystalline metal oxide particles, nanocrystalline metal hydroxide particles, doped nanocrystalline metal oxide particles and mixtures thereof.

3. The pouch of claim 2, wherein the nanocrystalline reactive particles comprise a coating.

4. The pouch of claim 2, wherein the nanocrystalline reactive particles comprise at least one halogen atom stabilized on the surfaces thereof.

5. The pouch of claim 1, wherein the fibrous matrix comprises a web of cellulosic fibers and the finely divided reactive particles comprise nanocrystalline metal oxide or metal hydroxide particles.

6. The pouch of claim 1, wherein the fibrous matrix comprises a web of cellulosic fibers and the finely divided reactive particles comprise nanocrystalline silver particles, or silver doped nanocrystalline metal oxides, or hydroxides particles.

7. The pouch of claim 1, wherein the fibrous matrix comprises a paper sheet of wet-laid wood pulp fibers.

8. The pouch of claim 1, wherein the fibrous matrix comprises a woven or non-woven textile material.

9. The pouch of claim 1, wherein the nanocrystalline particles are present in the sheet material at a concentration of from 1 to 90 percent by weight, based upon the total weight of the sheet material.

10. The pouch of claim 1, wherein the nanocrystalline particles are present in the sheet material at a concentration of from 25 to 75 percent by weight, based upon the total weight of the sheet material.

11. The pouch of claim 1, wherein the reactive nanocrystalline particles have a surface area of at least 15 $m^2/g$ and an average crystallite size of up to about 40 nm.

12. The pouch of claim 1, wherein the pouch comprises a closure for sealing said opening.

13. The pouch of claim 12, wherein the closure comprises a zipper-like structure.

14. The pouch of claim 1, wherein the barrier material comprises a multilayered film comprising one or more resins selected from the group consisting of polyvinyl chloride, chlorinated polyethylene, chlorinated butyl polyethylene, high density polyethylene, low density polyethylene, linear low density polyethylene, polypropylene, polyurethane, polytetrafluoroethylene (PTFE), ethylene-vinyl acetate, ethylene vinyl alcohol, polyvinyl alcohol, nylon, ionomer, and polyester.

15. The pouch of claim 1, wherein the barrier material is chemically resistant to one or more of sarin, mustard gas, lewisite, and soman.

16. The pouch of claim 1, wherein the sorptive sheet material has a size and shape that is configured to cover at least one side of the envelope.

17. A container for storing and transporting at least one contaminated item, comprising:
    top and bottom sheets affixed to each other to define a pouch having an interior space and an opening into the interior space, said top and bottom sheets comprising a multilayered barrier film that is impervious to gases and liquids,
    a sorptive sheet material disposed in the interior of said pouch, wherein said sorptive sheet material comprises a fibrous matrix and finely divided, nanocrystalline reactive particles dispersed within and bonded to the fibrous matrix, wherein contaminated fluids disposed in said container are absorbed into said fibrous matrix and react with said nanocrystalline particles.

18. The container of claim 17, wherein the container is in the form of a body bag.

19. The container of claim 17, wherein the top and bottom sheets are arranged in a juxtaposed relation and each including a top edge, a bottom edge, and opposite side edges, the sheets being interconnected along one of the side edges and along opposite top and bottom edges to define said interior space capable of receiving a contaminated item therein, and wherein the other side edges of the sheets are unconnected to form said opening into the interior space.

20. The container of claim 19, wherein the interconnected edges are hermetically sealed to each other.

21. The container of claim 17, wherein said sorptive sheet material substantially surrounds and lines an inner surface of said pouch.

22. The container of claim 17, wherein the container comprises structure for creating a gas-tight seal of said opening.

23. The container of claim 22, wherein the gas-tight seal comprises a hermetic seal.

24. The container of claim 22, wherein the gas-tight seal comprises a zipper-like structure.

25. A method of neutralizing an undesirable substance contained in a fluid comprising directing a fluid containing a member selected from the group consisting of chemical and biological agents, odors and odor causing compounds, and toxic industrial chemicals into the container of claim 17 and into contact with said sorptive sheet material.

26. A method of neutralizing an undesirable substance contained in a fluid emitted by a contaminated item comprising:
    introducing a contaminated item into the pouch interior space of the container of claim 17 via the pouch opening;
    positioning the contaminated item in contact with the sorptive sheet material disposed in the interior space of the pouch, wherein the sorptive sheet material comprises the paper substrate formed of cellulosic fibers and reactive nanocrystalline particles dispersed within the paper substrate and present at a concentration of from 1 to 90 percent by weight, based upon the total weight of the sheet material;

closing the opening of the pouch;

absorbing fluid emitted by the contaminated item into the sorptive sheet material; and reacting the undesirable substance contained in said fluid with said reactive nanocrystalline particles, the undesirable substance being a member selected from the group consisting of chemical and biological agents, odors and odor causing compounds, and toxic industrial chemicals.

27. The method of claim 26, wherein the contaminated item is a human body, animal body, bodily remains, or forensic sample.

28. The method of claim 26, wherein the step of closing the opening of the pouch comprises creating a hermetic seal across the opening.

29. A method of producing a container for storing and transporting at least one contaminated item comprising:

(a) forming an aqueous slurry containing cellulosic fibers and reactive nanocrystalline particles, depositing the slurry on a formanious wire and forming a sheet material therefrom, and drying the sheet material to produce a sorptive sheet material, (b) incorporating said sorptive sheet material into a pouch, wherein said pouch comprises top and bottom sheets affixed to each other thereby forming an interior space therebetween and an opening into the interior space, said top and bottom sheets comprising a multilayered barrier film that is impervious to gases and liquids, wherein said sorptive sheet material is disposed in the interior space of said pouch.

30. The method of claim 29, wherein the reactive nanocrystalline particles have a surface area of at least 15 $m^2/g$ and an average crystallite size of up to about 40 nm and are present in the slurry in an amount sufficient to produce a concentration of from 1 to 90 percent by weight, based upon the total weight of the dried sheet material.

* * * * *